United States Patent [19]

Imai et al.

[11] Patent Number: 4,913,883

[45] Date of Patent: Apr. 3, 1990

[54] PARTICLE AGGLUTINATION IMMUNOASSAY APPARATUS

[75] Inventors: Kazumichi Imai, Kodaira; Daizo Tokinaga, Hachioji; Koichi Yokosawa, Kokubunji, all of Japan

[73] Assignee: Hitachi, Ltd., Tokyo, Japan

[21] Appl. No.: 221,971

[22] Filed: Jul. 20, 1988

[30] Foreign Application Priority Data

Jul. 20, 1987 [JP] Japan ................................ 62-178895

[51] Int. Cl.$^4$ .................... G01N 30/96; G01N 33/553
[52] U.S. Cl. ................................... 422/82.01; 422/69; 436/526
[58] Field of Search ..................... 422/68, 69; 436/526

[56] References Cited

U.S. PATENT DOCUMENTS 4,661,408  4/1987  Peng et al. ......................... 428/405
4,663,277  5/1987  Wang ..................................... 435/5

Primary Examiner—Christine M. Nucker
Assistant Examiner—Karen I. Krupen
Attorney, Agent, or Firm—Pennie & Edmonds

[57] ABSTRACT

The degree of agglutination is measured in a magnetic manner instead of optical manner. Microparticles are composed of a magnetic material and the agglutinated condition is measured using a magnetometer. The sizes and distribution of agglutinated materials formed by the antigen-antibody coupling reaction can be correctly measured without affected by light-scattering materials such as proteins or blood cells contained in the specimen, or by absorbant such as pigment, or by fluorescent material. Therefore, the concentration of antigen is measured maintaining high precision.

11 Claims, 3 Drawing Sheets

PARTICLE AGGLUTINATION IMMUNOASSAY APPARATUS

BACKGROUND OF THE INVENTION

The present invention relates to a particle agglutination immunoassay apparatus employing a method of measuring particle sizes of agglutinated microparticles. More specifically, the invention relates to a particle agglutination immunoassay apparatus adapted to a determination method by applying the immunoagglutination reaction.

A method has heretofore been proposed according to which an antibody is coupled to the surfaces of microparticles such as latex beads and is reacted with a specimen to measure the amount of antigen in the specimen relying upon a difference in turbidity that changes depending upon the reaction. The principle is based upon the fact that the antigen on the surfaces of microparticles takes part in the antigen-antibody coupling reaction to agglutinate the microparticles and that the agglutination changes quantitative by with respect to the amount of the antigen. A variety of proteins have been determined based upon this method. With this method which measures at one time the whole reaction liquid having distribution in the agglutination degree, however, the average diameter only could be found leaving a problem with regard to precision for calculating the antigen concentration.

In order to solve this problem, there has been proposed a method in which the reaction liquid is dispersed for each agglutinated mass by the sheath flow method to measure the scattering intensity (journal of the Japanese Association of Automated Clinical Examination, 11, 1986, p. 226). According to this method, the agglutination degree of each of the agglutinated masses can be measured and the distribution of agglutination degrees can be measured, too, making it possible to improve the precision for calculating the antigen concentration.

Even in this method, however, the agglutination degree is measured in an optical manner and is inevitably affected by matters scattered in the specimen and absorbant such as pigment, imposing limitation on the measuring precision.

According to the above-mentioned prior art, no attention has been given to the effects caused by the matters scattered in the specimen, absorbant such as pigment or fluorescent material, giving rise to the occurrence of error in the measurement.

SUMMARY OF THE INVENTION

The object of the present invention is to solve the above-mentioned problem inherent in the prior art, and to provide a particle agglutination immunoassay apparatus which is capable of correctly measuring the sizes and distribution of the agglutinated particles formed by the antigen-antibody coupling and is capable of precisely finding the antigen concentration.

The above object is achieved by measuring the degree of agglutination in a magnetic manner instead of optical manner. That is, magnetic particles are used as microparticles and the agglutinated condition thereof is measured by adapting magnetic measuring means such as SQUID (superconducting quantum interference device) to the particle agglutination immunoassay apparatus.

According to the present invention, the antigen concentration is quantitatively measured according to the following method.

That is, antibody is coupled onto the surfaces of microparticles that can be magnetized, and the microparticles are reacted with antigen in a specimen. Masses of agglutinated particles develop accompanying the antigen-antibody coupling reaction.

The thus prepared reaction liquid for measurement is transferred into a sheath flow cell, and agglutinated masses of microparticles are dispersed and are moved together with the sheath liquid stream. The agglutinated masses in the liquid stream are magnetized and their magnetic moments are measured to quantitatively measure the antigen concentration.

Representative examples of microparticles that can be magnetized include metal particles such as of iron, nickel, cobalt and the like that have ferromagnetic properties. Gamma-ferrite particles and magnetite particles can be used with ease. It is further allowable to use particles obtained by applying the coating of such a material that can be magnetized.

The microparticles usually have particle sizes of smaller than about 2 $\mu$m. Preferably, the microparticles should have particle sizes of smaller than 1 $\mu$m. If the particle sizes are too small, the magnetic flux generated by the agglutinated mass becomes very weak. Therefore, the particle sizes are selected by taking into consideration the sensitivity of the magnetic measuring system and measuring ability such as signal-to-noise ratio and the like.

The antibody can be coupled to the surfaces of the microparticles relying upon the below-mentioned widely known means.

(1) Antibody is coupled by adsorption onto the surfaces of microparticles.

(2) After the antibody is coupled by adsorption onto the surfaces of microparticles, the antibody molecules are subjected to the chemical crosslinking. Owing to the crosslinking reaction, the microparticles and the antibody are coupled to each other more firmly than when the antibody is simply coupled by adsorption.

Examples of the crosslinking agent useful for the chemical crosslinking include bifunctional materials having aldehyde groups, carbodiimide groups and maleimide groups.

(3) The antibody is chemically coupled to the surfaces of microparticles.

(4) The surfaces of microparticles are coated with an organic high molecular material having functional groups such that the antibody is covalently bonded owing to the functional groups.

Polymethacrylic acid or the like is usually used as an organic high molecular material having functional groups.

Examples of the crosslinking agent used for effecting the chemical crosslinking include bifunctional materials that have aldehyde groups, carbodiimide groups and maleimide groups.

Preferred examples of the functional groups include amino groups, carboxyl groups, epoxy groups and hydroxyl groups.

The sheath flow cell may have an ordinary form such as the mechanism equivalent to the one adapted to, for example, the flow cytometer.

The detecting unit consists of a magnet for magnetizing microparticles and a magnetometer for measuring the magnetic moment, the magnetometer being desirably a SQUID (superconducting quantum interference device) magnetometer.

To accomplish the measurement maintaining a particularly high precision, the magnetometer consists of detection coils that are arranged in two to three directions that meet at right angles with each other.

Examples of the antigen to which the present invention can be adapted include human alpha-fetoprotein (AFP), carcino embrionic antigen (CEA), ferritin, $\beta_2$-microgrobulin ($\beta_2$-m), human corionic gonadotropin (HCG), C-reactive protein (CRP), and reumatoid factor.

By using magnetic particles as microparticles for coupling the antibody, the degree of agglutination of the agglutinated mass formed by the agglutination can be measured by measuring the magnetic moment. The measurement can be taken maintaining high precision since the measuring method is free from the aforementioned effects involved in the optical measurement.

DETAILED DESCRIPTION OF THE PREFERRED EMBODIMENT

Figure 1:
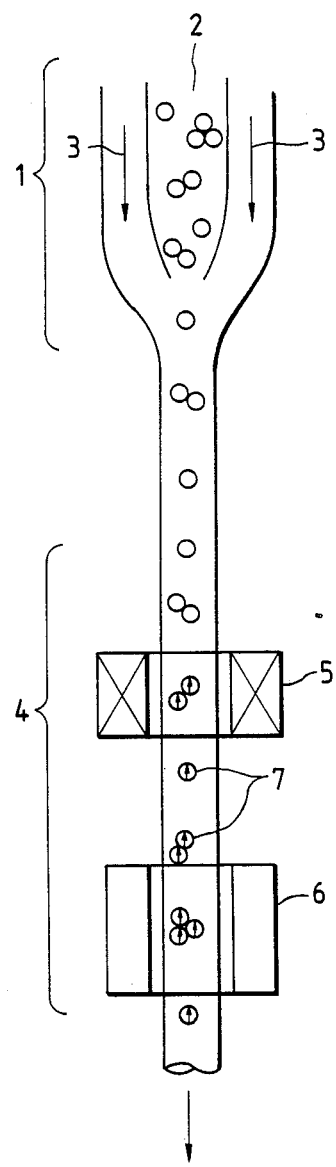
FIG. 1 is a schematic diagram illustrating the structure of an apparatus according to an embodiment of the present invention.

An embodiment of the present invention will now be explained in conjunction with FIG. 1.

Antihuman alpha-fetoprotein antibody (antihuman AFP antibody) was adsorbed onto the surfaces of spherical $\gamma$-ferrite particles (average particle diameter of 0.75 $\mu$m), and the antibody molecules were crosslinked using glutaldehyde to obtain fixed antibody magnetic beads. The fixing is accomplished by a widely known method such as the one disclosed in, for example, "Protein Hybrid" by Yuji Inada, Kyoritsu Shuppan Co. (Tokyo), 1987, pp. 119–122.

A suspension of the above-mentioned magnetic beads was added in an amount of 100 $\mu$l to 20 $\mu$l of serum that contained AFP at a variety of concentrations, and was reacted at room temperature for 15 minutes.

The reaction liquid was transferred to a liquid-detect unit 2 in a sheath flow cell 1, and the agglutinated mass in the reaction liquid was dispersed while flowing a sheath liquid 3 and was guided into a detecting unit 4. Though physiological saline solution was used as a sheath liquid, it is also allowable to use any suitable buffer solution or water. The sheath flow cell that is used has mechanism equivalent to the one applied to, for example, the flow cytometer. The flow path in the sheath flow cell has an inner diameter of 100 $\mu$m, and the flow rate of the sheath liquid and the pressure differential between the specimen and the sheath liquid were so set that the flow velocity was about 10 meters per second.

The agglutinated mass that was dispersed was guided into the detecting unit accompanying the flow.

The detecting unit 4 consists of a magnetic 5 for magnetization and a SQUID magnetometer 6.

The magnet 5 works to magnetize the microparticles. By using a ring-like electromagnet, the direction of magnetization can be oriented in one direction along the direction of flow. The direction of magnetization is indicated by arrows 7.

Figure 5:
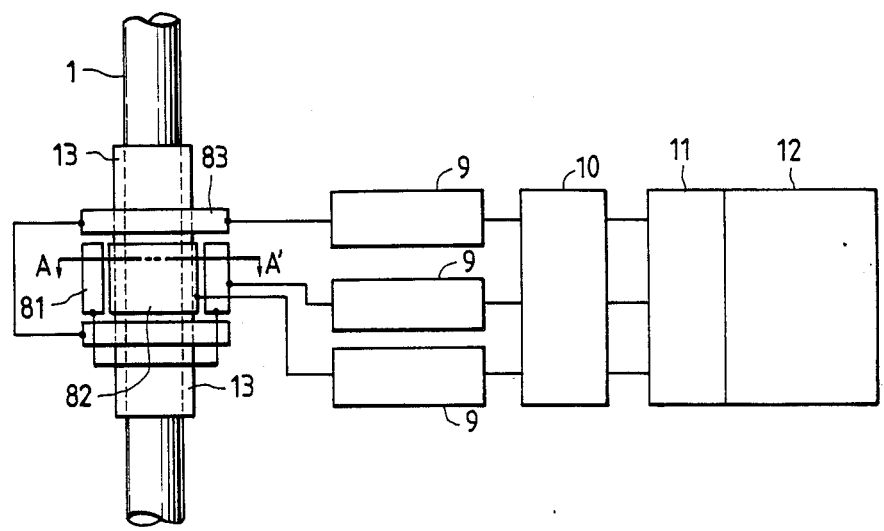
FIG. 5 is a diagram illustrating the structure of a magnetic measuring unit.
Figure 6:
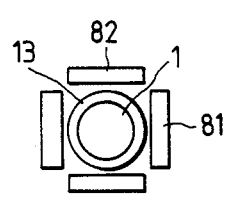
FIG. 6 is a section view illustrating part of the magnetic measuring unit.

The magnetometer 6 is a SQUID magnetometer constituted by arranging three pairs of detection coils in directions that meet at right angles with each other. FIG. 5 illustrates this condition. FIG. 6 is a section view along the line A–A' of FIG. 5. Coils are provided in two pairs (81, 82) on the side surfaces of the flow path 1 of the sheath flow cell and in one pair (83) in the direction at right angles with the direction of flow, in order to detect x-, y- and z-components of magnetic moment.

The detected signal value is subjected to the AD conversion through an A/D converter and is guided into a personal computer 12 which calculates the square root of the sum of square values of the signals to find the intensity of the magnetic moment. Owing to this processing in which a mass of microparticles to be measured rotates, no error develops in the measured values that was always involved so far when the component in one direction only of the magnetic moment was detected.

In order to simplify the apparatus, furthermore, the detection coils may be arranged in one direction only or in two directions only to take measurement.

Figure 7:
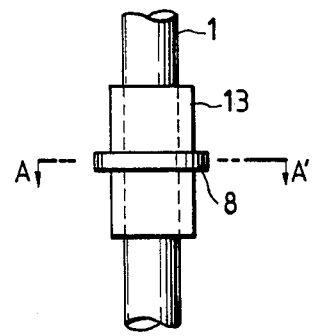
FIG. 7 is a diagram illustrating another structure of the magnetic measuring unit.
Figure 8:
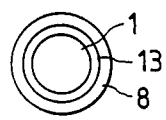
FIG. 8 is a section view illustrating part of the magnetic measuring unit of FIG. 7.

FIG. 7 is a diagram illustrating the arrangement of coils for simplifying the structure of the apparatus, and FIG. 8 is a section view along the line A–A' of FIG. 7. In these drawings, one pair of detection coils are used. In this case, attention must be given such that the mass of microparticles will not rotate, and error caused by rotation must also be taken into consideration.

Examples of the superconducting material for the SQUID may be oxide superconducting materials. For instance, use can be made of high-temperature superconducting materials of the oxygen-deficient perovskite structure expressed by the general formula $RE_{1-x}2M_{x/2}X_uO_{3-x}$ or of the $K_2NiF_4$ structure.

In the above general formula, RE represents such element as lanthanum, yttrium, strontium, ytterbium, lutetium, thulium, dyprosium, scandium, cerium, proseodymium, neodymium, samarium, europium, gadolinium, terbium, holium, erbium, or the like, and M represents such element as barium, strontium, calcium, potassium or the like.

In order to obtain superconducting condition according to this embodiment, the SQUID (detection coils as well as SQUID) is used being cooled with liquid nitrogen. To prevent the flow cell portion from freezing, furthermore, a heat-insulating material 13 having good permeability is disposed between the detection coil and the flow cell.

Using the above high-temperature superconducting material, it becomes easy to effect the cooling and heat insulation or to preclude the need therefor.

Figure 2:
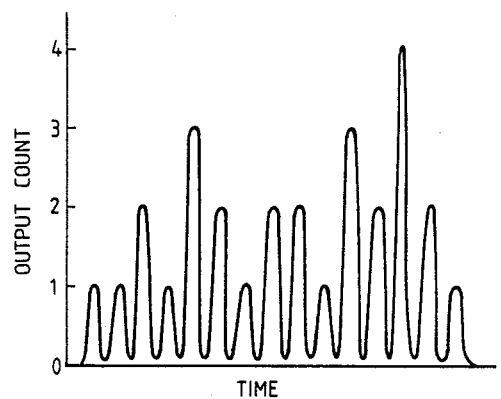
FIG. 2 is a diagram illustrating detect signals.
Figure 3:
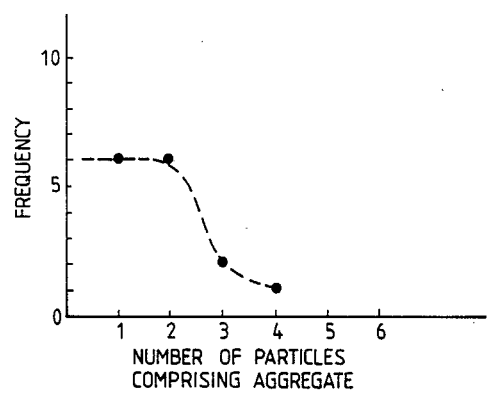
FIG. 3 is a diagram illustrating the measurement of particle size distribution.
Figure 4:
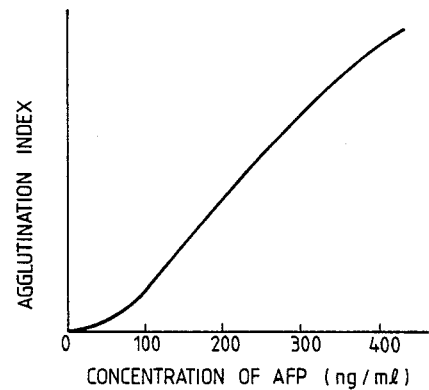
FIG. 4 is a diagram illustrating the measurement of AFP.

By measuring the magnetic moment of the agglutinated masses using the magnetometer 6, it becomes easy to find the number of microparticles (agglutination degree) of the individual agglutinated masses. At the same time, distribution of the agglutination degrees can also be found. The measured results are shown in FIGS. 2 and 3. With reference to FIG. 2, magnitude of the output signal varies depending upon the number of particles collected in the agglutinated mass.

Relying upon the agglutination degree, the agglutination ratio is found by calculating the ratio of agglutinated masses consisting of two or more microparticles.

$$\text{Agglutination ratio} = \frac{\text{Number of agglutinated masses containing two or more microparticles}}{\text{Number of agglutinated masses}}$$

Similarly, the AFP was measured in the blood (containing red blood cells) treated with heparin. The size of the agglutinated mass could be correctly measured without any problem, and a correlation curve same as that of the case of serum was obtained.

According to this embodiment, therefore, the agglutinated condition of the microparticles due to the antigen-antibody coupling reaction can be measured without affected by absorbant or light-emitting material such as light-scattering material and pigment that exist in the specimen.

The embodiment is also effective for the measurement of hemolysis specimens and chlemia serum specimens.

The present invention makes it possible to correctly measure the sizes and distribution of agglutinated matters formed by the antigen-antibody reaction without affected by the light-scattering material such as proteins and blood cells contained in the specimen, or by the absorbant such as pigment or by fluorescent material. Therefore, the antigen concentration can be measured maintaining precision.

What is claimed is:

1. A particle agglutination immunoassay apparatus that measures the concentration of antigen in a specimen by measuring the agglutination of microparticles formed by the reaction of said antigen with antibody coupled to the surfaces of microparticles, the improvement comprising:

means which disperses agglutinated masses of microparticles formed by the reaction and moves the agglutinated masses together with the flow of liquid; and detect means which magnetically measures the sizes of agglutinated masses in the flow of liquid.

2. A particle agglutination immunoassay apparatus according to claim 1, wherein the antibody is coupled by adsorption to the surfaces of microparticles.

3. A particle agglutination immunoassay apparatus according to claim 1, wherein the antibody is adsorbed onto the surfaces of microparticles, and then the antibody molecules are coupled through chemical cross-linking.

4. A particle agglutination immunoassay apparatus according to claim 1, wherein the antibody is chemically coupled to the surfaces of microparticles.

5. A particle agglutination immunoassay apparatus according to claim 1, wherein the surfaces of microparticles are coated with organic high molecules having functional groups, and the antibody is covalently bonded by using the functional groups.

6. A particle agglutination immunoassay apparatus according to claim 1, wherein the microparticles are composed of a material that can be magnetized.

7. A particle agglutination immunoassay apparatus according to claim 6, wherein the material that can be magnetized is a ferromagnetic material.

8. A particle agglutination immunoassay apparatus according to claim 6, wherein the material that can be magnetized is a metal.

9. A particle agglutination immunoassay apparatus according to claim 1, wherein the detecting unit consists of a magnet for magnetizing the microparticles and a magnetometer for measuring the magnetic moment.

10. A particle agglutination immunoassay apparatus according to claim 9, wherein the magnetometer is a SQUID magnetometer.

11. A particle agglutination immunoassay apparatus according to claim 10, wherein the magnetometer is comprised of detection coils that are arranged in two to three directions that meet at right angles with each other.

* * * * *